United States Patent [19]

Cobb

[11] 4,070,576

[45] Jan. 24, 1978

[54] DETECTING MALIGNANT CELLS

[75] Inventor: Carolus M. Cobb, Arlington, Mass.

[73] Assignee: American Science & Engineering, Inc., Cambridge, Mass.

[21] Appl. No.: 654,178

[22] Filed: Feb. 2, 1976

[51] Int. Cl.² .............................................. G01T 1/161
[52] U.S. Cl. ..................................... 250/303; 250/304
[58] Field of Search ................................ 250/303, 304

[56] References Cited

U.S. PATENT DOCUMENTS

| 3,673,410 | 6/1972 | Waite et al. | 250/303 X |
| 3,801,783 | 4/1974 | Caiola | 250/303 |
| 3,857,033 | 12/1974 | Cobb | 250/303 |

Primary Examiner—Archie R. Borchelt
Attorney, Agent, or Firm—Charles Hieken

[57] ABSTRACT

The detection of malignant or dysplastic cells in a tissue sample, by treating the sample with a solution containing radioactive gallium and relying upon the greater take-up of the gallium by the malignant or dysplastic cells relative to normal cells to provide a detectable signal of malignancy, is improved by including non-radioactive preemptive species in the solution to pre-empt potential gallium binding sites in protein molecules of normal cells. The pre-emptive species may be one or more of scandium, indium or yttrium.

4 Claims, 10 Drawing Figures

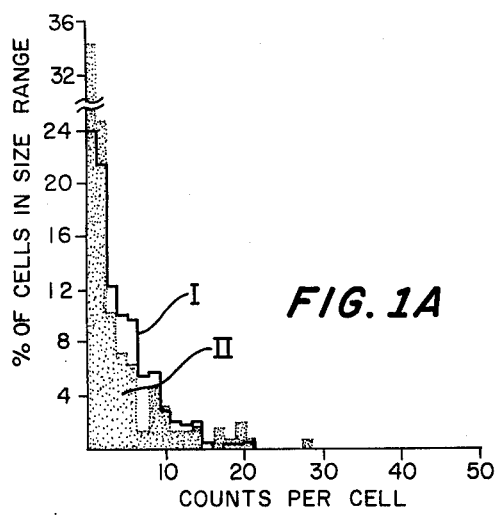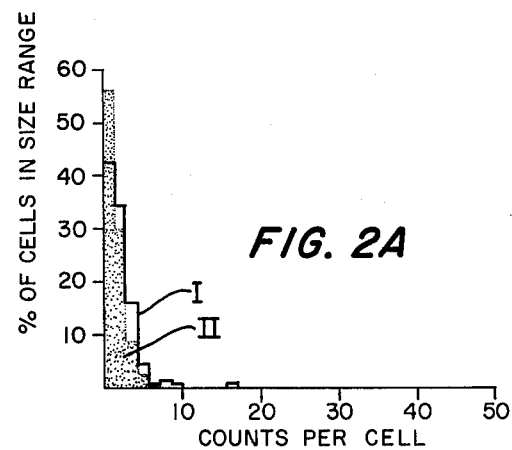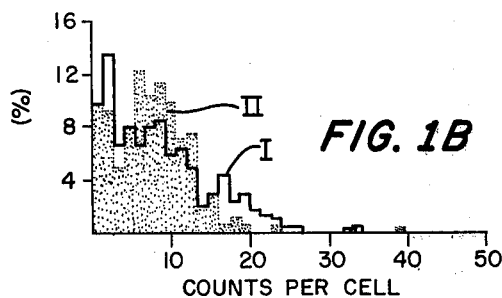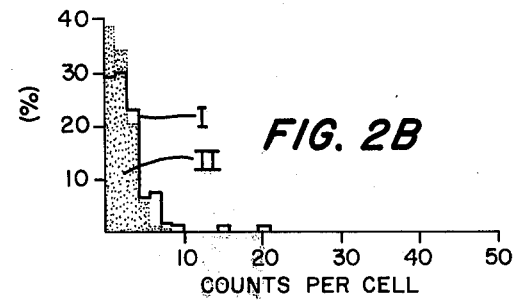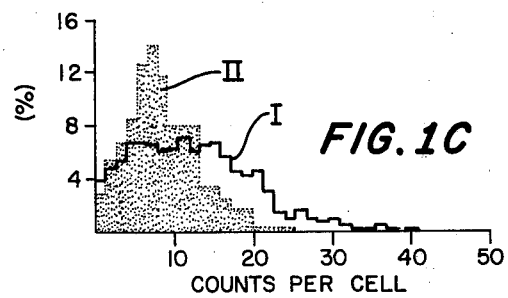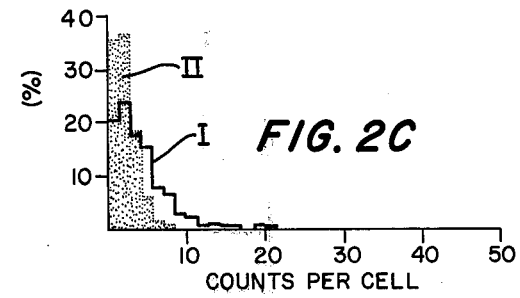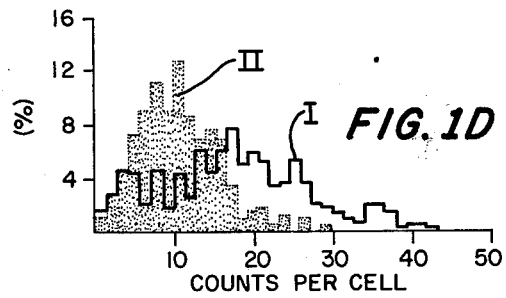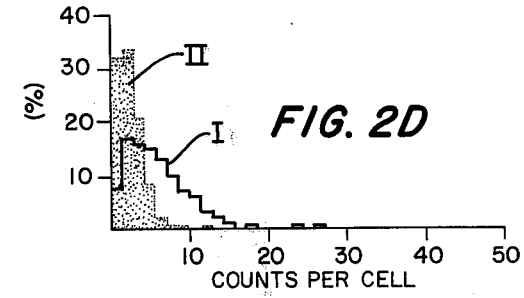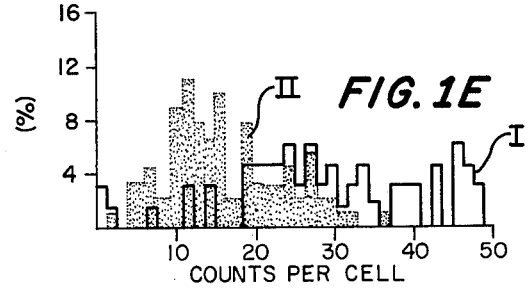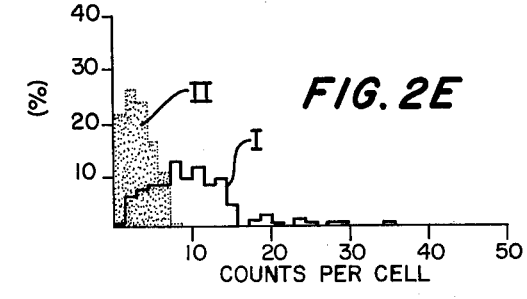

DETECTING MALIGNANT CELLS

BACKGROUND OF THE INVENTION

The present invention relates in general to detecting cell conditions and more particularly to detection of malignant or dysplastic cells by inducing absorption of radioactive gallium from an inoculant solution by a tissue sample which may contain malignant or dysplastic cells together with normal cells and subsequently measuring gallium content of the cells using radioactivity detection methods to produce signals correlatable with the number of malignant or dysplastic cells in the tissue sample because of the tendency of the malignant or dysplastic cells to preferentially absorb the gallium relative to absorption by the normal cells. It is a particular feature of the invention that the sensitivity of such processing is substantially enhanced, through modification of the inoculation solution, without substantial increase of cost, processing steps, or calibration effort. Such benefits in sensitivity are particularly useful in connection with automating the cell examination process phase of the Papanicolau (PAP hereinafter) smear analysis process.

Non-automated PAP test processing involves smearing scrapings from the cervix upon a slide. The slide is stained with several dyes and a trained cytotechnician observes the slide under a microscope looking for cells meeting criteria of malignancy. One slide examination typically takes a technician 15 minutes for a negative specimen. Typically, there are only 55 positives in 10,000 specimens. When positives are detected, a cytopathologist is consulted. Present manual testing procedures of pre-screening by cytotechnicians involve substantial wasted time of these skilled and expensive personnel. The state of the art on automation of PAP smear analysis to eliminate, in substantial part, the cost and time delays of sample processing are described in "Summary of State-of-the-Art Workshop on Papanicolau Smear Analysis," edited by Ramsey-Klee in April, 1970, available from the Clearing House for Federal Scientific and Technical Information, Springfield, Va. and National Technical Information Service, Washington, D.C.; prior U.S. Pat. No. 3,912,929 granted Oct. 14, 1975 and U.S. Pat. No. 3,857,033 granted Dec. 24, 1974, and references therein cited, all of which are incorporated herein by reference. U.S. Pat. No. 3,912,929 particularly describes automated cell-by-cell examination comprising formation of a solution containing radioactive gallium and suspending a cell population to be tested in the gallium, flowing the test suspension through a cell counter and scintillation counter in an arrangement providing cell by cell series array in the flow, measuring radioactive emission of each cell and accumulating radioactive decay counts and cell numbers in a fashion convertible to a histogram plot of number of cells against counts per cell of decay incidents.

It is an important object of the invention to improve automated tissue examination by increasing the sensitivity, accuracy and speed thereof.

It is a further object of the invention to increase the uptake of radioactive tracer material by abnormal cells consistent with the preceding object.

It is a further object of the invention to suppress, at least in part, uptake of radioactive tracer by normal cells consistent with one or more of the preceding objects.

SUMMARY OF THE INVENTION

In accordance with the present invention, the solution for inoculating radioactive tracer material into cells of a tissue sample suspended therein is modified by provision of a competing pre-emptive species in the solution to preempt binding of the tracer to normal cells. The pre-emptive species is selected as having crystallographic radii and Pauling electronegativity values which are very close to those of the radioactive tracer species within a ratio of 1:1.5 to 1.5:1. In connection with use ofgallium as a radioactive tracer, the appropriate pre-emptive species are preferably scandium, indium and yttrium. The crystallographic radii and Pauling electronegativity for gallium and these other ions are listed in Table I below:

TABLE I

| Ion | Crystallographic Radius (A) | Electronegativity |
|-----|-----------------------------|-------------------|
| $Ga^{+3}$ | 0.62 | 1.8 |
| $Sc^{+3}$ | 0.81 | 1.4 |
| $In^{+3}$ | 0.81 | 1.8 |
| $Y^{+3}$ | 0.92 | 1.2 |

The pre-emptive species, scandium, indium and yttrium do not compete well with gallium for reaction sites in the abnormal material because their ionic sizes are larger, and in the case of scandium and yttrium, their binding energies are somewhat weaker. The pre-emptive species react to a greater extent with potential gallium binding sites in protein molecules of normal cells, such as terminal glycine type sites.

The pre-emptive species are used in excess in comparison to the radioactive tracer species, preferably in excess by a ratio factor (of formula weight of pre-emptive species to formula weight of radioactive species per liter) of at least 1,000 times.

The radioactive species and pre-emptive species may be applied to the solution as salts thereof. Solvents for the solution may comprise ethanol, xylene, and other common solvents known to those skilled in the art.

The tissue samples are handled to vitro, with the benefits compared to prior to vivo sampling as discussed in my above cited U.S. patents The radioactive and pre-emptive species may both comprise other elements or compounds subject to the same considerations indicated above illustratively for gallium and scandium/indium/yttrium.

These and other objects, features and advantages of the invention will be apparent from the following detailed description with reference therein to the accompanying drawing in which:

BRIEF DESCRIPTION OF THE DRAWING

FIGS. 1A–1E and 2A–2E each contain histograms of cell count (as percent of total population) vs. radioactive decay counts from samplings of cells taken from normal and abnormal patients under conditions described in Example I below.

DETAILED DESCRIPTION OF PREFERRED EMBODIMENTS

The following non-limiting examples illustrate the practice of the invention and demonstrate its viability for cell analysis.

EXAMPLE I

Cell samples were taken by scraping the cervix of female patients with a dry spatula. Certain patients were known to have a carcinoma in situ and other patients were known to be normal. The samples were immediately placed in alcohol. Upon delivery to a laboratory, the samples were resuspended by shaking on a vortex mixer, diluting with additional alcohol and freeing large aggregates by passing the alcohol through a screen with a 53 micron pore size. Scandium is added to the solution as scandium trichloride in the amount of 100 $\mu$g/ml of alcohol, corresponding to $2.2 \times 10^{-3}$ formula weight of scandium per liter of solution. The ratio of formula weights of scandium to gallium was at least $2.2 \times 10^{-3}$ to $1.3 \times 10^{-8}$, i.e., $1.7 \times 10^{+5}$. Detergent is added to the solution along with the cell sample to prevent cell clumping. The mixture is allowed to stand for several hours. A measured portion of the screened, filtered call sampling containing about 50,000 cells is set aside.

A gallium solution is prepared as follows. The gallium $-67$ is initially obtained as gallium trichloride dissolved in dilute hydrochloric acid. The solution is then diluted to standard activity of 800 to 2000 microcuries per ml with ethyl alcohol corresponding to about $2.01 \times 10^{-8}$ to $5.00 \times 10^{-8}$ formula weights of gallium per liter. The pH of the solution (70–90 volume percent alcohol) is adjusted by sodium hydroxide addition to about pH3. The solution is then filtered through a 0.2 micron filter prior to insertion of a cell sample therein.

An aliquot of the 67 gallium solution containing 100 to 3000 (or greater) microcuries is added to the cellular solution and the final ratio of scandium to gallium is adjusted to:

$$\frac{100 \text{ micrograms/ml Sc}}{50 \text{ to } 1000 \text{ microcuries/ml Ga}}$$

or an equivalent formula weight ratio, $$\frac{2.22 \times 10^{-3} \text{Sc}}{1.25 - 2.50 \times 10^{-8} \text{Ga}} = 1.78 \times 10^6 \text{ to } 8.88 \times 10^4$$

The cells are then repeatedly flushed with filtered alcohol until the radiation level in the supernatent liquid is low enough to give no measurable background in a scintillation counter and resuspended in carrier fluid. The fluid is then injected into a sample beaker and pumped therefrom past a cell counter and scintillation counter. The flow is controlled so that the cells pass the cell counter essentially one-by-one. Cell count and scintillation data are taken and automatically processed in the manner disclosed, for example, in U.S. Pat. No. 3,912,929.

Histograms were plotted from the cell count and scintillation count data taken using cell samples taken from a patient (I) known to have a carcinoma in situ and a patient (II) known to be normal and the above described sample preparation technique excepting that separate sets of samples were prepared with and without scandium addition. Histograms were plotted from data taken by testing the cells as described above and are shown in FIGS. 1A–1E for samples tested without scandium and FIGS. 2A–2E for samples tested with scandium addition which are correlatable to tested samples as follows:

FIGS. 1A and 2A are for cells of 5–7 $\mu$m avg. diameter

FIGS. 1B and 2B are for cells of 7–10 $\mu$m avg. diameter

FIGS. 1C and 2C are for cells of 10–15 $\mu$m avg. diameter

FIGS. 1D and 2D are for cells of 15–25 $\mu$m avg. diameter

FIGS. 1E and 2E are for cells of 25–150 $\mu$m avg. diameter

Each figure contains a histogram I for the patient with carcinoma and a histogram II for the normal patient.

In FIGS. 1A–1E and 2A–2E, the histograms reflect normalization of data to constant time and innoculation concentration and representation of numbers of cells as percentages of total cell population.

The histograms I and II of FIGS. 2A–2E all show depressed uptake of gallium compared to corresponding histograms in FIGS. 1A–1E, but the effect is consistently greater for histograms II.

The following table gives the ratios of normalized average cellular gallium$^{-67}$ activity(in average counts per cell) of a sample from patient I to that of a sample from patient II with and without scandium present in the inoculating solutions.

| Diameter Size Range ($\mu$m) | 5 – 7 | 7 – 10 | 10 – 15 | 15 – 25 | 25 – 50 |
|---|---|---|---|---|---|
| Ratio without Scandium | 0.78 | 1.2 | 1.5 | 1.8 | 2.0 |
| Ratio with Scandium | | 1.5 | 4.2 | 5.8 | 5.2 |

It can be seen that in the size ranges greater than 10 $\mu$m, the ratio of average gallium$^{-67}$ uptake has increased by about a factor of 2.5 for these samples when scandium is used in the inoculation solutions.

It is evident that those skilled in the art, once given the benefit of the foregoing disclosure, may now make numerous other uses and modifications of, and departures from the specific embodiments described herein without departing from the inventive concepts. Consequently, the invention is to be construed as embracing each and every novel feature and novel combination of features present in, or possessed by, the apparatus and techniques herein disclosed and limited solely by the scope and spirit of the appended claims.

What is claimed is:

1. Cytological examination method comprising,
    suspending a cell population in a carrier fluid together with a radioactive tracer species which is linkable to both normal and abnormal cells, but more readily to one than the other, in essentially repeatable differential uptake pattern,
    further incorporating in said such suspension a pre-emptive species which pre-emptively links to the type of cell which is less readily linked by the tracer species to enhance the pattern of differential uptake of tracer by suspended cells,
    and measuring radioactivity of separate portions of the cell population to produce decay count data based on extent of tracer pickup by each such portion, wherein the tracer species is gallium and the preemptive species is selected from the class consisting of indium, yttrium and scandium.

2. Cytological examination method in accordance with claim 1 where said pre-emptive species is scandium.

3. Cytological examination method in accordance with claim 1 wherein said separate cell portions comprise single cells.

4. Cytological examination method in accordance with claim 1 wherein the formula weight ratio of pre-emptive species to tracer species in said fluid is at least 1000:1.

* * * * *